United States Patent [19]

Pauli et al.

[11] 4,087,543

[45] May 2, 1978

[54] COMPOSITION FOR DISINFECTING SOIL AND COMBATING PLANT DISEASES CONTAINING ORGANIC DICARBONATES

[75] Inventors: Otto Pauli; Hermann Genth, both of Krefeld; Hermann Wolz, Leverkusen, all of Germany

[73] Assignee: Bayer Aktiengesellschaft, Leverkusen, Germany

[21] Appl. No.: 654,671

[22] Filed: Feb. 2, 1976

[30] Foreign Application Priority Data

Feb. 15, 1975 Germany .............................. 2506482

[51] Int. Cl.² .......................... A01N 9/02; A01N 9/24
[52] U.S. Cl. ..................................... 424/301; 424/311
[58] Field of Search ................................ 424/301, 311

[56] References Cited

U.S. PATENT DOCUMENTS

| 1,599,809 | 9/1926 | Cohen et al. ........................ 424/301 |
| 2,910,400 | 10/1959 | Bernhard et al. ................... 424/301 |
| 3,186,906 | 6/1965 | Genth .................................... 424/301 |
| 3,920,847 | 12/1975 | Chalaust .............................. 424/301 |

OTHER PUBLICATIONS

McCutcheon, Detergents and Emulsifiers (1963) p. 156.
Agriculture Handbook No. 340; Aug. 1967; pp. 7 & 184.

*Primary Examiner*—Allen J. Robinson
*Attorney, Agent, or Firm*—Burgess, Dinklage & Sprung

[57] ABSTRACT

Composition for disinfecting soil and combating plant diseases containing 85 to 98 per cent by weight of an organic dicarbonate, 0.1 to 15 per cent by weight of an alkylphenyl polyethyl glycol and 0.01 to 5.0 per cent by weight of a halogenoformic acid ester and/or 0.1 to 5.0 per cent by weight of dialkyl carbonate.

10 Claims, No Drawings

COMPOSITION FOR DISINFECTING SOIL AND COMBATING PLANT DISEASES CONTAINING ORGANIC DICARBONATES

BACKGROUND

This invention relates to a composition containing organic dicarbonates and its use for soil disinfection and combating plant diseases.

The use of pyrocarbonic acid esters (organic dicarbonates) as preservatives for perishable materials is known from German Published Specification No. 1,011,709. However, the use of organic dicarbonates in plant protection did not appear possible, particularly because of their property - highly desirable in preserving foodstuffs - of reacting quantitatively and irreversibly, within a few hours, with compounds which contain active hydrogen atoms, and in the presence of water, to give physiologically harmless reaction products.

It has been disclosed to employ diethyl dicarbonate (DEDC) in greenhouses, before or after planting of seedlings, in order to disinfect the soil or disinfect the seed (Report 1969 of the Horticultural Research Institute of Ontario, pages 99 – 104).

However, in attempting to use diethyl dicarbonate for the disinfection of soil, it was found that in each case an undesirable and adverse change in the soil texture resulted, which can be described as a hardening or encrusting of the upper layer of the soil. In many cases, furthermore, only an inadequate or intermittent effect was found, which was attributable to a decomposition of the diethyl dicarbonate in the ethyl alcohol stock solution or in the aqueous watering solution prepared therefrom. This was because for the experiments, as described in the above-mentioned literature reference, page 100, diethyl dicarbonate was first dissolved in 95% strength ethyl alcohol and then suitably diluted with water. The decomposition of diethyl dicarbonate in alcoholic solution has already been known for a considerable time (compare Baycovin for the Cold Sterilisation of Beverages, pages 4 and 5, BAYER Company Leaflet, 1964).

Furthermore, it was found that the change in the soil texture is attributable to the alcohol content of the watering solution used.

Accordingly, a composition containing organic dicarbonates which does not contain any alcohol and in which the organic dicarbonate remains stable over a long period was sought. This is because, for practical use, it is essential that in particular the concentrate should retain its full activity over prolonged periods, since special storage measures require too much labour. Furthermore, it is necessary to ensure complete solution of the organic dicarbonate since the undiluted organic dicarbonates frequently cause plant damage.

SUMMARY

It has now been found that these requirements are fulfilled by a composition which contains 85 to 98 percent by weight of an oganic dicarbonate, 0.1 to 15 percent by weight of an alkylphenyl polyethylene glycol, and 0.01 to 5.0 percent by weight of a halogenoformic acid ester and/or 0.1 to 5.0 percent by weight of a dialkyl carbonate.

DESCRIPTION

The organic dicarbonates used in the invention are known; they correspond in general to the formula

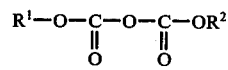

in which

R$^1$ and R$^2$ are identical or different and represent alkyl, cycloalkyl, phenyl or benzyl.

Alkyl radicals which may be mentioned are straight-chain or branched radicals with up to 6 C atoms, preferably with up to 4 C atoms; possible radicals are methyl, ethyl, propyl, isopropyl, butyl and isobutyl, pentyl radicals such as amyl and isoamyl and the isomeric hexyl radicals.

Cyclopentyl and cyclohexyl may preferentially be mentioned as cycloalkyl e.g. containing 5 or 6 carbon atoms in the ring.

Preferably, diethyl dicarbonate (diethyl- dicarbonic acid ester) and dimethyl dicarbonate are used.

It is also possible to use mixtures of different organic dicarbonates of the formula I, especially mixtures of dimethyl dicarbonate and diethyl dicarbonate.

The halogenoformic acid esters according to the invention correspond to the formula

in which

Hal represents halogen and

R$^3$ represents a straight-chain or branched alkyl radical with 1 to 4 carbon atoms.

Halogens which may be mentioned are fluorine, chlorine, bromine and iodine, preferably chlorine; chloroformic acid alkyl esters are used in particular because of their easy accessibility.

Alkyl radicals with 1 to 4 carbon atoms which may be mentioned are methyl, ethyl, propyl, isopropyl, butyl, isobutyl and tert.-butyl, preferably methyl, ethyl and propyl.

The dialkyl carbonates according to the invention are also known and in general correspond to the formula

in which

R$^4$ and R$^5$ are identical or different and represent a straight-chain or branched alkyl radical with 1 to 4 carbon atoms.

As has been mentioned, mixtures of different dicarbonates of the formula I can also be used; equally, it is possible to use mixtures of different halogenoformic acid esters of the formula II and mixtures of different dialkyl carbonates of the formula III.

The alkylphenyl polyglycol ethers used in invention are also known; they correspond in general to the formula

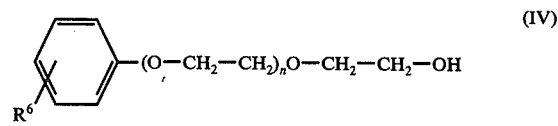

in which
R[6] denotes an alkyl radical with 4 to 20, preferably 8 to 12, carbon atoms and
n represents a number from 4 to 30.

The alkylphenyl polyglycol ethers according to the invention can be obtained in a known manner by reaction of alkylphenols of the formula

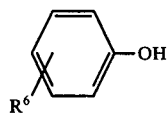 (V)

in which
R[6] has the abovementioned meaning,
with 5 to 31 mols of ethylene oxide.

Suitable alkyl radicals R[6] are straight-chain and branched alkyl radicals of the stated number of carbon atoms, but preferably straight-chain alkyl radicals with 8 to 12 C atoms, especially the nonyl radical.

Preferably, a nonylphenyl polyglycol ether which is obtained in the usual manner by reaction of nonylphenol with about 10 mols of ethylene oxide is employed.

The composition according to the invention has an exceptionally high shelf life of more than 12 months, in general at least about 24 months, virtually without a chemical reaction of the organic dicarbonate and therefore without a decrease in action or loss of action.

The composition according to the invention can be used as follows:

Sufficient water is added to the composition of the invention, hereafter referred to for brevity as the concentrate, that a solution which is in general from 0.05 to 3 percent strength by weight, preferably a solution of about 0.1 to 0.2 percent strength by weight, with regard to the amount of the organic dicarbonate contained in the aqueous solution, is produced.

The solutions thus obtained are clear solutions which can easily be applied by watering, spraying and atomising. They are in particular active against moulds, yeasts and bacteria and can especially also be used for combating Fusariosis and food rot, resp. root rot. The composition of the invention can be used with advantage, in the form of the solution described above, for the single-treatment disinfection of horticultural soil or agricultural soil, without any problems of residues. Sensitive flower seed, such as, for example, those of chrysanthemums, carnations, lobelias or cyclamen can then be developed in this soil without attack by microbes and can thus be guided through the most sensitive phase of germination without undergoing infection. Furthermore, watering of cuttings or young plants with the use solution, described above, of the agent according to the invention, in this stage of growth, is a particularly suitable method of preventing frequently occurring fungal and/or bacterial diseases of the plants or, if an infection has already occurred, reducing their severity to the point that during the further development of the plants damage is not detectable and the commercial utilisation of the plants, for example through sale, is not handicapped. The composition of the invention can furthermore be used especially advantageously for particularly sensitive young plants and for flowering plants, even if the blossoms are already open. This was tested, for example, in the case of carnations, freesias and cyclamen, without occurrence of damage to leaf and blossom and without handicapping the saleability of the plants.

The particular advantage of the composition of the invention over the state of the art relating to the use of pyrocarbonic acid esters resides, as already mentioned, in the better shelf life of the agent according to the invention compared to the organic dicarbonates per se. As a result of not using alcohol to prepare the concentrate or an alcoholic stock solution, no decrease in action as a result of the abovementioned alcoholysis of the dicarbonate can occur. Furthermore, the composition of the invention possesses very good wetting strength and adhesion, which is particularly important for the treatment of the plants, while an aqueous-alcoholic solution of diethyl dicarbonate according to the state of the art possesses no wetting capacity. Thus, for the first time it is possible to use an organic dicarbonate for protecting the growing and living plant in a lasting manner, and using little of the composition, against an infection which does not take place through the soil and/or against a disease which has already occurred.

At the same time, the use of the composition of the invention does not result in any undesired side-effects. There is neither a change in the consistency of the soil — no hardening, no sticking together and no disintegration of the previously existing structure of the soil occurs — nor is there an adverse effect on the germination of the seed and the growth of the plants, nor damage to the plant, which would be detectable, for example, from the occurrence of leaf blotches.

Furthermore, the process of the invention does not result in complete sterilisation of the soil, which would be undersirable in many cases, but only in a substantial reduction in the number of phytopathogenic microbes, so that controlled combating of plant diseases is possible without eliminating the normal and necessary soil microflora.

In using the composition of the invention it is not necessary to prepare alcoholic stock solutions and the watering solutions can be made up directly; this results in a saving in material and working time.

The following concentrates were used in the examples which follow:

Concentrate A: 96% by weight of dimethyl dicarbonate, 2% by weight of chloroformic acid methyl ester and 2% by weight of nonylphenol polyglycol ether-10.

Concentrate B: 92% by weight of diethyl dicarbonate, 2% by weight of chloroformic acid ethyl ester, 2% by weight of chloroformic acid methyl ester, 2% by weight of diethyl carbonate and 2% by weight of nonylphenol polyglycol ether-30.

Concentrate C: 40% by weight of dimethyl dicarbonate, 55% by weight of diethyl dicarbonate, 2% by weight of dimethyl carbonate, 1% by weight of chloroformic acid n-propyl ester and 2% by weight of nonylphenol polyglycol ether-20. Notes:

In the case of the nonylphenol polyglycol ether, the figure hyphenated to the word ether indicates the approximate number of mols of ethylene oxide which were used to prepare the polyether.

EXAMPLE 1

The concentrates A, B and C were stored at a temperature of 20° to 25° C and were analysed, at irregular intervals, for their content of organic dicarbonate.

Over the course of a storage time of 12 months, no decrease in the content of organic dicarbonate was observed.

The storage and examination of the concentrate B was continued over a further 12 months, that is to say over a total of 24 months, without it being possible to detect a decrease in the content of organic dicarbonate.

EXAMPLE 2

Normal horticultural soil from a greenhouse contained $5 \times 10^9$ bacteria per g and $2 \times 10^9$ moulds per g. It was watered with 2 liters per m² of an 0.1% strength by weight aqueous solution of the concentrate B. After about 10 hours (because of the time required for the determination, the renewed determination was carried out between 8 and 12 hours later) the number of bacteria had fallen to $2 \times 10^2$ and the number of moulds to $3 \times 10^3$, in each case per g of soil. A reduction in the number of bacteria to $2 \times 10^1$ and of the moulds to $3 \times 10^1$, in each case per g of soil, was achieved by using 4 liters, instead of 2 liters, of the 0.1% strength by weight aqueous solution per m².

EXAMPLE 3

Horticultural soil was watered for 12 hours using a watering can with an 0.1% strength by weight aqueous solution of the concentrate A at a dosage of 2 liters per m² before sowing salvia seed. The seed germinated more uniformly than in the case of untreated horticultural soil, and without any infection.

EXAMPLE 4

Young lobelia plants were planted out in horticultural soil which had been watered with 2 liters per m² of an 0.1% strength by weight aqueous solution of the concentrate A, by means of a watering can, 10 hours before starting the planting work.

The plants which had been planted out grew on substantially better than in untreated soil and suffered no infection by Fusarium culmorum, whilst of the plants planted out in untreated soil, 4% showed delayed growth, and 8% had failed completely, after 2 weeks, as the result of infection by Fusarium colmorum.

EXAMPLE 5

Chrysanthemum cuttings were planted in soil which had been watered, using a watering can, with 1 liter of an 0.1% strength by weight solution of the concentrate A per m², 8 hours after watering. After 6 weeks, the better growth of the cuttings could be seen, and there was neither damage nor delay in blossom formation with the very sensitive young plants; in the comparison group planted in untreated soil, 2 – 3% of the plants were removed as infected and 1% of the plants as showing deformed growth.

EXAMPLE 6

Carnation cuttings and bromelia cuttings were planted in soil which had been watered with 2 liters of an 0.1% strength by weight aqueous solution of the concentrate B. The Fusarium infection amounted to 0% of the plants, whilst comparison plants in untreated soil were infected to the extent of 14%.

EXAMPLE 7

Freshly germinated lobelia seed which had been sown in untreated horticultural soil was watered directly with 2 liters of an 0.1% strength by weight aqueous solution of the concentrate C per m². On evaluation after 10 – 14 days, all seed had germinated and remained uninfected. The failure rate in untreated comparison experiments was between 5 and 10%.

EXAMPLE 8

4 month old cyclamen plants were watered directly with 2 liters, and in another group with 4 liters, per m², of an 0.1% strength by weight aqueous solution of the concentrate A. All treated plants thrived well and showed no infection by harmful microbes. Of the untreated comparison group, 2% of the plants were infected and were not utilisable.

EXAMPLE 9

Young freesia plants were watered directly once with an 0.1% strength by weight aqueous solution of the concentrate B at the rate of 2 liters per m², and once at the rate of 4 liters per m², and at the end of 30 minutes were re-watered with about 1 liter of water per m². Thereafter, a marked regression of the Fusariosis, compared to the comparison plants, was observed with 98% of the plants, and better growth was observed with 20% of the plants.

If fully grown fressia plants were watered directly with 2 liters of an 0.1% strength by weight aqueous solution of the concentrate A per m², no damage resulted, even if the plants were subsequently not watered with water alone.

What is claimed is:

1. A composition for disinfecting soil and combating plant diseases caused by moulds, yeasts or bacteria, comprising (1) 85 to 95 percent by weight of an organic dicarbonate having the formula

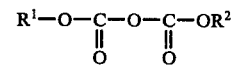

wherein $R^1$ and $R^2$ are the same or different and are alkyl having up to 6 carbon atoms, cyclopentyl, cyclohexyl phenyl or benzyl, (2) 0.1 to 15 percent by weight of an alkylphenyl polyglycol ether having the formula

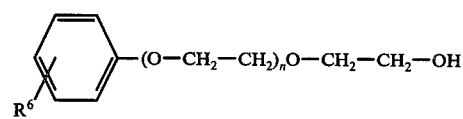

wherein $R^6$ is alkyl with 4 to 20 carbon atoms and $n$ is a number from 4 to 30, and (3) 0.01 to 5.0 percent by weight of a halogenoformic acid ester of the formula

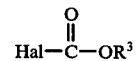

wherein Hal is halogen and $R^3$ is alkyl having up to 4 carbon atoms.

2. A composition of claim 1 wherein the organic dicarbonate has the formula

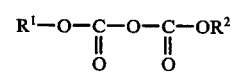

wherein
$R^1$ and $R^2$ are the same or different and are alkyl having up to 4 carbon atoms, cyclopentyl, cyclohexyl, phenyl or benzyl.

3. A composition of claim 1 wherein the alkylphenyl polyglycol ether has the formula

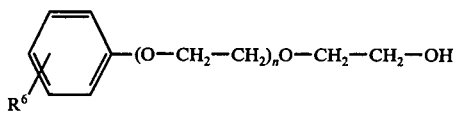

wherein
R$^6$ is alkyl with 8 to 12 carbon atoms and
n is a number from 4 to 30.

4. A composition of claim 1 wherein the halogenoformic acid ester has the formula

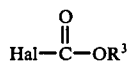

wherein
Hal is chlorine and
R$^3$ is alkyl having up to 4 carbon atoms.

5. A composition of claim 1 wherein the organic dicarbonate is dimethyl dicarbonate.

6. A composition of claim 1 wherein the organic dicarbonate is diethyl dicarbonate.

7. A composition of claim 1 additionally containing 0.1 to 5.0 percent by weight of dialkyl carbonate of the formula

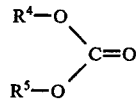

in which R$^4$ and R$^5$ are the same or different and represent alkyl with 1 to 4 carbon atoms.

8. A process for disinfecting soil and combating plant diseases caused by moulds, yeasts or bacteria which comprises applying an effective amount of a composition of claim 1 to soil to be disinfected or to diseased plants.

9. A process of claim 8 for disinfecting soil and combating plant diseases caused by Fusariosis.

10. A process of claim 8 for disinfecting soil and combating plant diseases caused by food rot.

* * * * *